(12) United States Patent
Koh

(10) Patent No.: US 7,082,638 B2
(45) Date of Patent: Aug. 1, 2006

(54) ELECTRO-MOTION TOOTHBRUSH

(76) Inventor: Kyung-Yong Koh, 107-405, Chyoung-Gu Apt., Banghak 4-Dong, Dobong-Gu, Seoul (KR)

( * ) Notice: Subject to any disclaimer, the term of this patent is extended or adjusted under 35 U.S.C. 154(b) by 433 days.

(21) Appl. No.: 10/450,520

(22) PCT Filed: Dec. 12, 2001

(86) PCT No.: PCT/KR01/02146

§ 371 (c)(1),
(2), (4) Date: Jul. 7, 2003

(87) PCT Pub. No.: WO02/47512

PCT Pub. Date: Jun. 20, 2002

(65) Prior Publication Data

US 2004/0128777 A1    Jul. 8, 2004

(30) Foreign Application Priority Data

Dec. 12, 2000  (KR) ............................. 2000-75571

(51) Int. Cl.
*A61C 17/26*  (2006.01)
(52) U.S. Cl. ...................................... 15/22.1; 15/167.2
(58) Field of Classification Search ............... 15/22.1, 15/167.2, 22.2; 601/129
See application file for complete search history.

(56) References Cited

U.S. PATENT DOCUMENTS

| | | | | | |
|---|---|---|---|---|---|
| 5,177,827 | A | * | 1/1993 | Ellison | ................ 15/22.1 |
| 5,617,603 | A | * | 4/1997 | Mei | ................ 15/22.1 |

FOREIGN PATENT DOCUMENTS

| | | |
|---|---|---|
| JP | 48-17075 | 2/1973 |
| JP | 62-281906 | 12/1987 |
| JP | 7-1823 | 1/1995 |

OTHER PUBLICATIONS

PCT International Search Report for International Application No. PCT/KR01/02146; International filing date: Dec. 12, 2001.
PCT Notification of Transmittal of International Preliminary Examination Report for International Application No. PCT/KR01/02146; Dec. 12, 2001.

* cited by examiner

*Primary Examiner*—Gladys J. P. Corcoran
*Assistant Examiner*—Shay L. Balsis
(74) *Attorney, Agent, or Firm*—Cantor Colburn LLP

(57) ABSTRACT

The present invention relates to an electromotive toothbrush and more particularly, to an electromotive toothbrush, comprising upper and lower tooth covers surrounding and covering upper and lower teeth, respectively, and having bristles formed at a surface contacting the teeth; a first driving rod combined with a surface of the upper and lower tooth covers where there are no bristles; a second driving rod combined with a left side of a surface of the upper and lower tooth covers where there are bristles; a third driving rod combined with a left side of a surface of the upper and lower tooth covers where there are bristles; a plurality of sensors independently sensing positions of the first, second, and third driving rods; reciprocation means driving the first driving rod and the second and third driving rods in opposite directions to move the upper and lower tooth covers in opposite directions and thereby clean the teeth, the reciprocation means driven by power supplied from a motor, in response to position information sensed by the plurality of sensors.

13 Claims, 16 Drawing Sheets

(a)

(b)

(c)

ELECTRO-MOTION TOOTHBRUSH

FIELD OF THE INVENTION

The present invention relates to an electro-motion toothbrush, and more particularly, an electro-motion toothbrush covering all of the teeth while the electro-motion toothbrush cleans the teeth automatically.

DESCRIPTION OF THE RELATED ART

Generally, a manual toothbrush has a rod shape, wherein one end of the rod is implanted by lots of bristles, and the other end of the rod is a handle. When cleaning the teeth, a user grips the handle and brushes the bristles to the teeth for cleaning the teeth. Such a manual toothbrush has some disadvantages in that the user has to move his hands to the direction of teeth cleaning without ceasing.

To solve such a problem, an electro-motion toothbrush is developed to clean teeth more easily by the method that an electric motor rotates or drives the bristles of the electro-motion toothbrush automatically when the bristles are contacted with his teeth.

When the user cleans his teeth by the conventional electro-motion toothbrush, the user has to move his hands to the direction of teeth cleaning without ceasing like the manual toothbrush.

In other words, even though an electric motor drives the bristles automatically, the conventional electro-motion toothbrush can not clean all of the teeth simultaneously. Therefore, when using the electro-motion toothbrush, the user has to place the bristles to the clean-required teeth like the manual toothbrush. Accordingly, even though the conventional electro-motion toothbrush is simple in cleaning the teeth, comparing with the manual toothbrush, full cleaning for all of the teeth can be accomplished by the user's selection like the conventional manual toothbrush.

Therefore, even though the conventional electro-motion toothbrush is driven automatically to clean the teeth, full cleaning for all of the teeth can be accomplished by the user's considerable attentions to gaps between the teeth or to the boundary between the teeth and the teeth-ridge. Because most users do not clean corners of the teeth, such a problem can not be solved in the case of using the conventional electro-motion toothbrush.

SUMMARY OF THE INVENTION

In order to achieve the above object, the preferred embodiments of the present invention provide an electro-motion toothbrush comprising: a upper and lower tooth cover surrounding and covering upper and lower teeth, respectively, and having bristles formed at a surface contacting the teeth; a first driving rod combined with a surface of the upper and lower tooth covers where there are no bristles; a second driving rod combined with a left side of a surface of the upper and lower tooth covers where there are no bristles; a third driving rod combined with a right side of a surface of the upper and lower tooth covers where there are no bristles; a plurality of sensors independently sensing positions of the first, second, and third driving rods; reciprocation means driving the first driving rod and the second and third driving rods in opposite directions to move the upper and lower tooth covers in opposite directions and thereby clean the teeth, the reciprocation means driven by power supplied from a motor, in response to position information sensed by the plurality of sensors.

In more, the upper and the lower bottom tooth covers include a joint plate combined with the first driving rod, the second driving rod, and the third driving rod.

In more, the upper and the lower tooth covers include a plurality of bristles plates adhesively combined together, each of the plates implanted with bristles.

In more, concave regions of the top and the bottom tooth covers include projection regions for making the bristles contacted with molars of the teeth.

In more, the motor and the reciprocation means are provided inside a handle. The reciprocation means includes a first reciprocation means disposed on the axis of rotation of the motor and reciprocating the first driving rod up and down when the motor rotates. The reciprocation means further includes a second reciprocation means disposed on the axis of rotation of the motor and reciprocating the second and third driving rods up and down in the opposite direction to the first driving rod when the motor rotates.

In more, the rotation axis of the motor comprises: a first eccentric unit, bent in one direction and rotated eccentrically, providing an eccentric force to the first reciprocation means; and a second eccentric unit, bent in the other direction and rotated eccentrically, providing an eccentric force to the second reciprocation means.

In more, the first reciprocation means comprises: a first reciprocation ring, including a long hole extending in one direction into which the first eccentric unit; and a first extension rod extending from the first reciprocation ring, supported by the inside of the handle, and combined with the first driving rod, and wherein the second reciprocation means comprises: a second reciprocation ring including a long hole extending in one direction into which the second eccentric unit; and a second extension rod extending from the second reciprocation ring, supported by the inside of the handle, and combined with the second and the third driving rods.

In more, the first and a second reciprocation rings are provided inside the handle, and the first and second guide grooves are provided at both ends of the first or second reciprocation rings for guiding up/down movement of the first and the second reciprocation rings.

In more, the motor is a static rotation motor.

In more, the first and second reciprocation rings are provided inside the handle, and the first reciprocation means includes a first piston extendable in both directions according to direction of reciprocation, both ends of the first piston are supported by the inside of the handle, and the first eccentric unit is fitted on the side of the first piston; and wherein the second reciprocation means includes a second piston extendable in both directions according to direction of reciprocation, both ends of the second piston supported by the inside of the handle, and the second eccentric unit is fitted on the side of the second elevation piston.

In more, the first driving rod includes: a plurality of first upper branch rods combined with the inside of the upper tooth cover; and a plurality of first lower branch rods combined with the inside of the lower tooth cover.

In more, the second driving rod includes a second upper branch rod combined with the left outside of the upper tooth cover, and a second lower branch rod combined with the left outside of the lower tooth cover; and wherein the third driving rod includes a third upper branch rod combined with the right outside of the upper tooth cover, and a third lower branch rod combined with the right outside of the lower tooth cover.

In more, each of the driving rods can be attached together or detached from one another.

In more, the reciprocation means comprises a sensor detecting a position of each of the driving rods.

In more, the tooth covers are molded by a shape memory alloy in a body.

BRIEF DESCRIPTION OF THE DRAWINGS

These and other objects, features and advantages of the present invention will become more understood from the following detailed description of the preferred embodiment thereof made with reference to the accompanying drawings, in which like reference numerals denote like parts, and of which.

DETAILED DESCRIPTION OF PREFFERED EMBODIMENTS

Reference will now be made in detail to preferred embodiments of the present invention, example of which is illustrated in the accompanying drawings.

Figure 1:
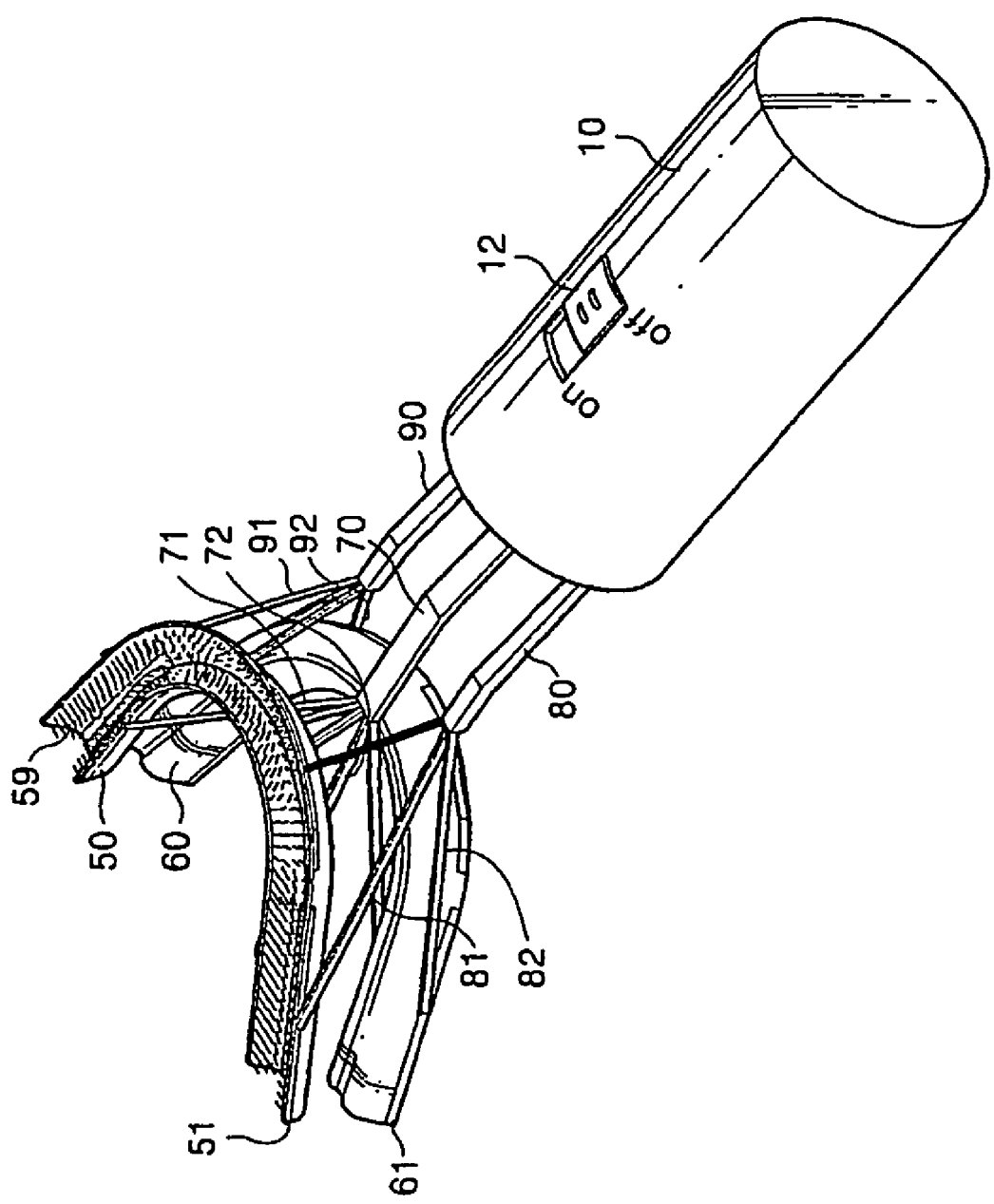
FIG. 1 is a perspective view illustrating an electro-motion toothbrush according to the preferred embodiment of the present invention.

Referring to FIG. 1, the electro-motion toothbrush of the present invention comprises a handle 10, having a size griped by a hand and a cylindrical shape, and three driving rods 70, 80 and 90 projected into the front side of the handle 10. The handle 10 has a mode switch 12 for operating the electro-motion toothbrush or for changing a detachable tooth cover illustrated in the following statement.

The electro-motion toothbrush of the present invention also comprises a top and a bottom tooth covers 50 and 60, and an elevation means (not shown) of the handle 10. The top and the bottom tooth covers 50 and 60 are combined with each of the driving rods 70, 80, and 90, for covering the upper teeth, in other name, maxillary teeth, and the lower teeth, in other name, mandibular teeth, respectively. The elevation means moves up and down each of the driving rods 70, 80 and 90.

Figure 2:
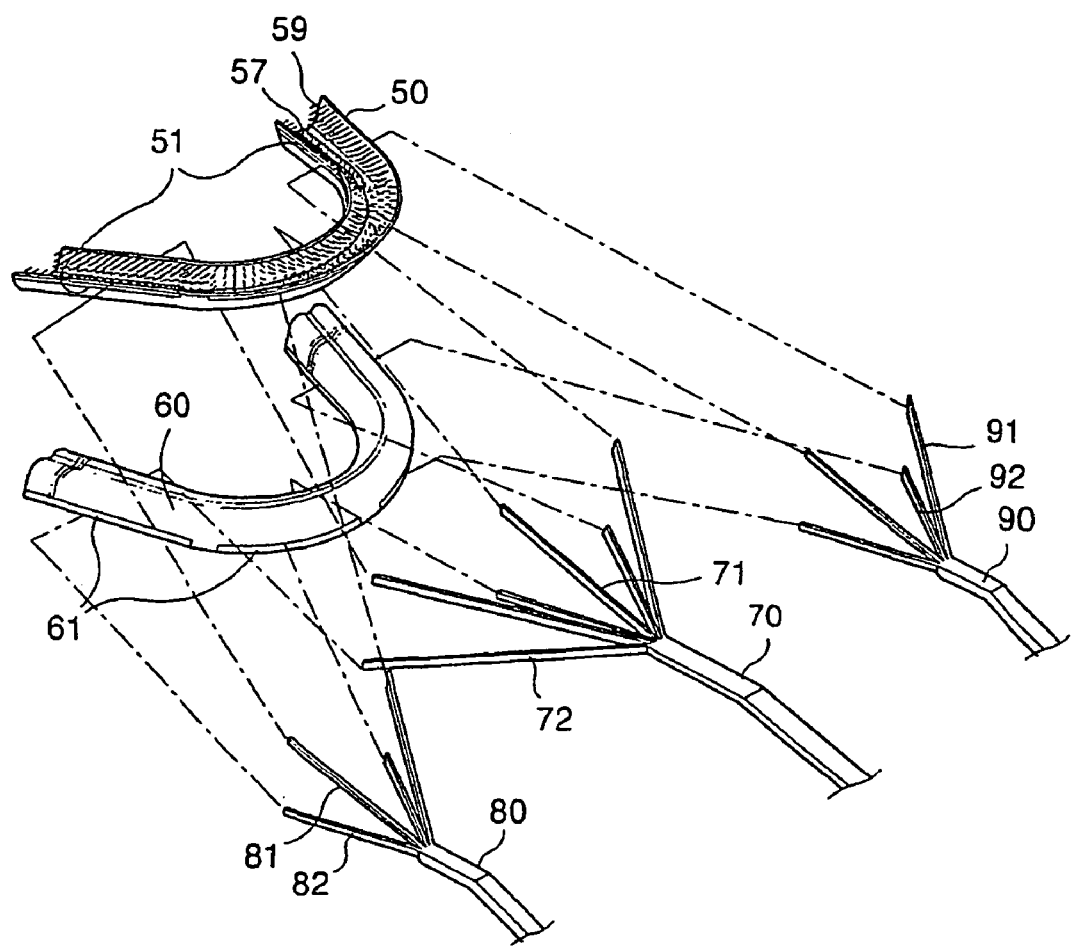
FIG. 2 is a magnified perspective view illustrating a driving rod combined with the tooth cover of the electro-motion toothbrush of the present invention.
Figure 3:
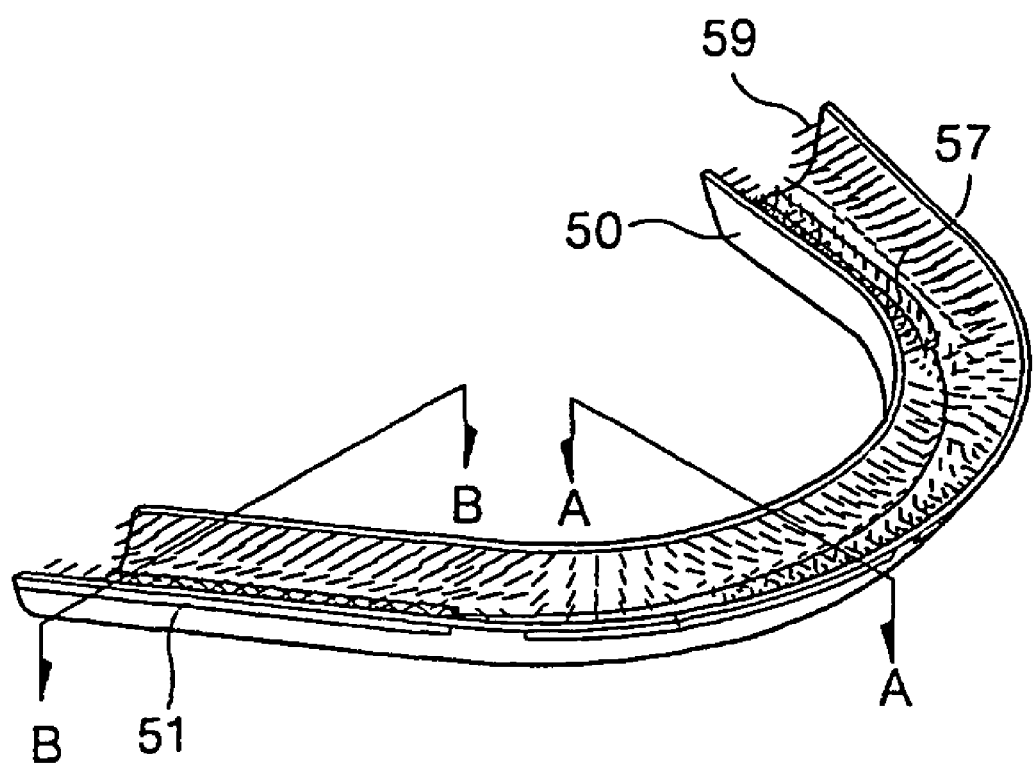
FIG. 3 is a magnified perspective view illustrating a tooth cover of the electro-motion toothbrush of the present invention.

In more detail, referring to FIG. 2, the top and the bottom tooth covers 50 and 60 have a rounded semi-lunar end for enclosing simultaneously all of the teeth, such as a foretold and a molar, and the inside of the semi-lunar end includes bristles 58 of about 2~3 mm length.

In more, multiple joint plates 51 and 61 are installed in outsides of the top and the bottom tooth covers 50 and 60, and combined with the above described driving rods 70, 80 and 90. The tooth covers 50 and 60 are made of silicon materials, and each of the joint plates 51 and 61 is manufactured by a normal injection molding method.

In the middle and both ends of an inner top side of the top tooth cover 50, the joint plate 51 comprises a $1^{st}$ top joint plate, $2^{nd}$ top joint plate, and a $3^{rd}$ top joint plate, respectively. In more, In the middle and both ends of the outer upper side of the top tooth cover 50, the joint plate 51 comprises a $4^{th}$ top joint plate, a $5^{th}$ top joint plate, and a $6^{th}$ top joint plate, respectively.

Sequentially, the joint plate 61 comprises a $1^{st}$ bottom joint plate, $2^{nd}$ bottom joint plate, and a $3^{rd}$ bottom joint plate in the middle and both ends of an inner bottom side of the bottom tooth cover 60, respectively. In more, the joint plate 61 comprises a $4^{th}$ bottom joint plate, a $5^{th}$ bottom joint plate, and a $6^{th}$ bottom joint plate in the middle and both ends of an outer bottom side of the bottom tooth cover 60, respectively.

Figure 4:
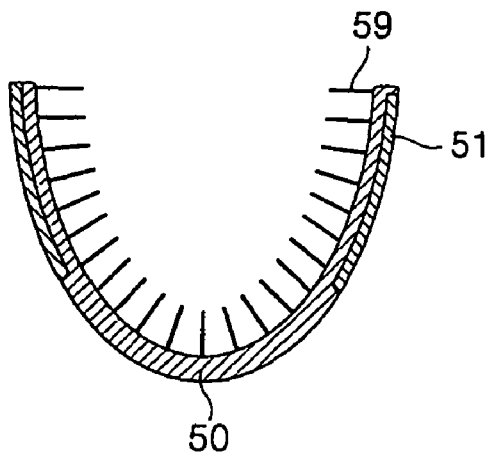
FIG. 4a is a cross sectional diagram according to A—A line of FIG. 3.
FIG. 4b is a cross sectional diagram according to B—B line of FIG. 3.
FIG. 4c is a cross sectional diagram illustrating a tooth cover of the electro-motion toothbrush according to other preferred embodiment of the present invention.
Figure 4:
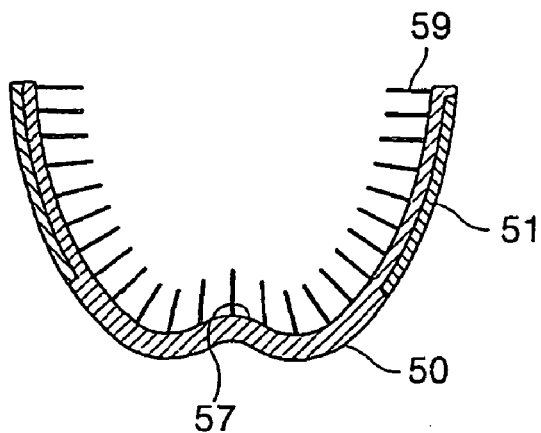
Figure 4:
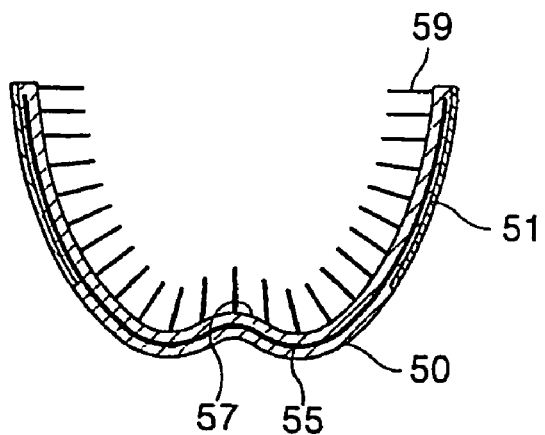

Additionally, as shown in FIG. 4a and FIG. 4b, the joint plate 51 is apart from both ends of the top tooth cover 50 in a distance of about 1~2 mm, and the joint plate 61 is also apart from both ends of the bottom tooth cover 60 in a distance of about 1~2 mm. Therefore, it is hard for teeth-ridges to contact directly with the joint plates 51 and 61, and be damaged while tooth brushing.

The forepart of the top tooth cover 50 is designed to lift up to the upward direction. This is a result of consideration for opening the mouth when the top tooth cover 50 is fitted to the teeth.

On the contrary, projection units 57 are protruded to the inner circular direction from the side end units of the top tooth cover 50 and the bottom tooth cover 60, respectively. The projection units 57 make an upper planar portion of the molars contacted with the bristles 59 closely for being cleaned completely.

Figure 5:
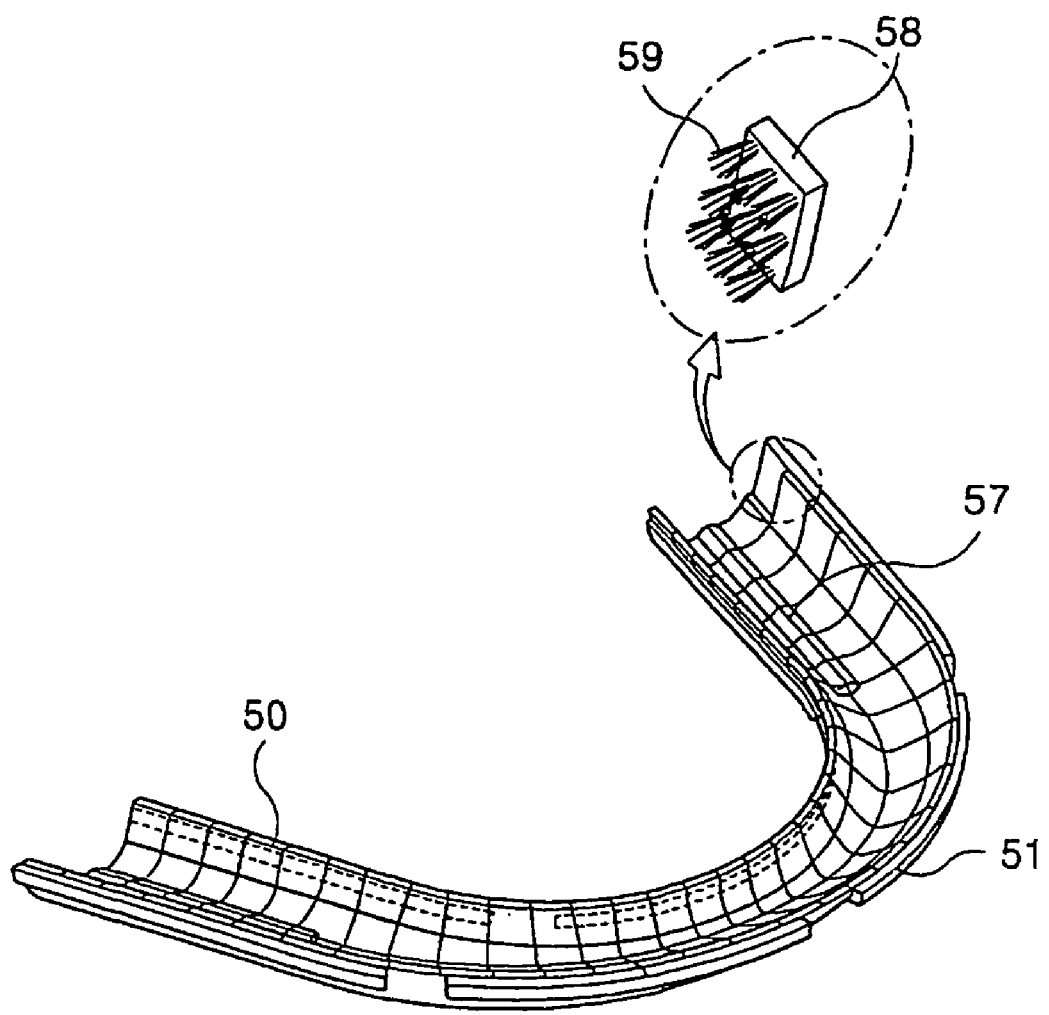
FIG. 5 is a magnified perspective view illustrating a tooth cover of the electro-motion toothbrush according to another preferred embodiment of the present invention.
Figure 6:
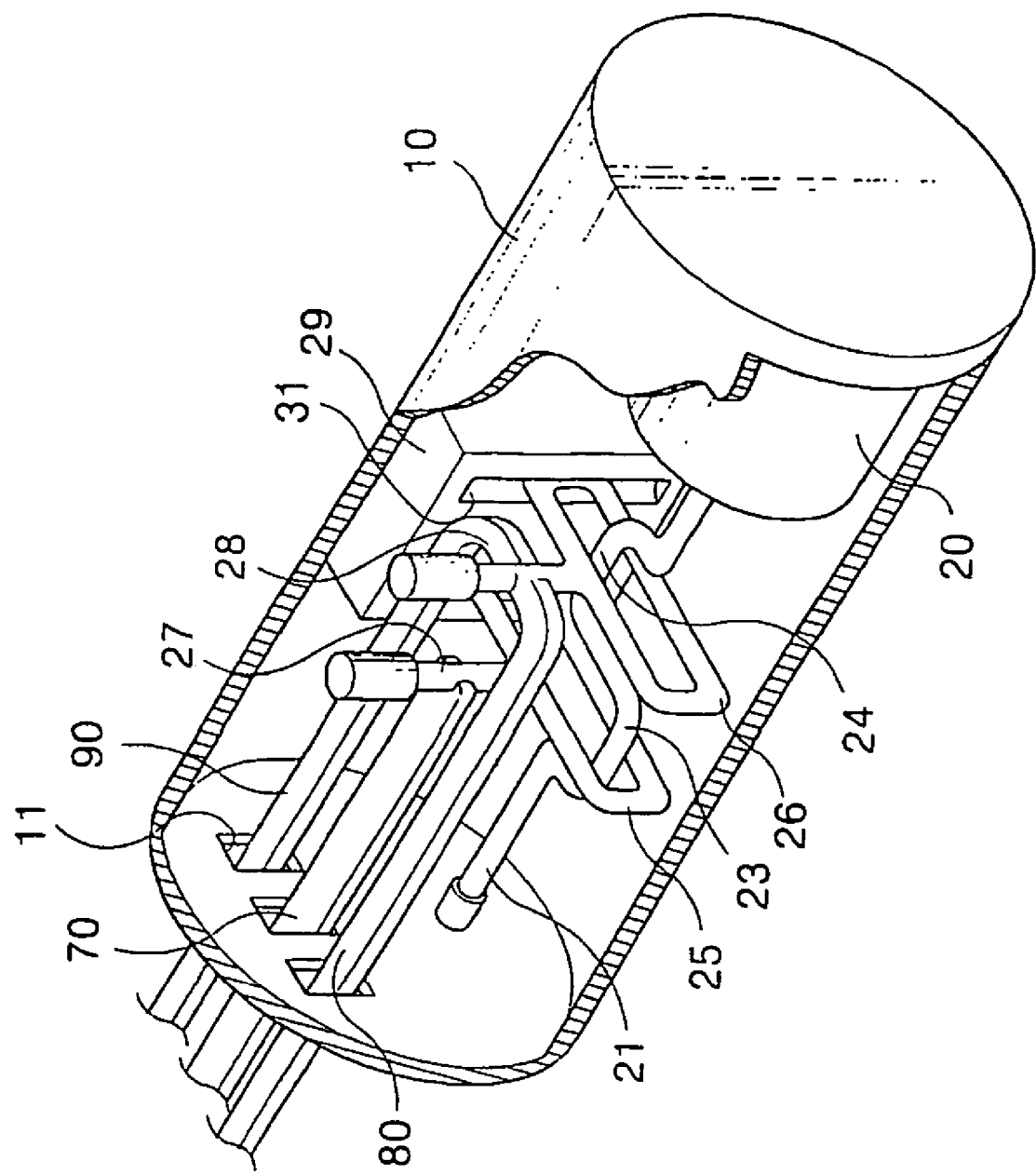
FIG. 6, FIG. 7 and FIG. 8 are magnified detail perspective views for driving rods of an electro-motion toothbrush, illustrating operation states of each of the driving rods.

Each of the tooth covers 50 and 60 can be prepared by silicon materials through the injection molding method, and can be also prepared by assembling individual bristle turfs 58, shaped in rectangular, embedding lots of bristles 59 as shown in FIG. 5. An adhesive can be applied in the side of the bristle turfs 58, so that the bristle turfs 58 are assembled together.

As shown in the above statement, after average size of the teeth is calculated according to one's age, the standard model of the tooth covers 50 and 60 can be produced on a large scale. However, the size and the shape of the tooth covers 50 and 60 can be variable according to one's age and teeth states for better teeth management and for better usage efficiency of the tooth covers 50 and 60. In this case, the individual bristle turfs 58 can be applied as the above described descriptions.

The driving rods 70, 80 and 90 comprise a first driving rod 70 placed on the middle of the tooth covers 50 and 60, and a second and a third driving rods 80 and 90 placed on the both sides of the tooth covers 50 and 60.

The end of the first driving rod 70 comprises 6 isolation rods, wherein 3 first top isolation rods 71 are prolonged to the upward direction of the inner side of the top tooth cover 50, and wherein 3 first bottom isolation rods 72 are prolonged to the downward direction of the inner side of the bottom tooth cover 60.

Each of the first top isolation rods 71 is combined with a first top joint plate, a second top joint plate, and a third top joint plate among the joint plate 51 of the top tooth cover 50, respectively. In more, each of the first bottom isolation rods 72 is combined with a first bottom joint plate, a second bottom joint plate, and a third bottom joint plate among the joint plate 51 of the bottom tooth cover 60.

Therefore, when the first driving rod 70 moves up and down, the inner sides of the top tooth cover 50 and the bottom tooth cover 60 move to the direction of the first driving rod 70.

The end portion of the second driving rod 80 comprises four isolation rods, wherein two top isolation rods 81 are combined with the outer left sides of the top tooth cover 50, and wherein two bottom isolation rods 82 are combined with the outer left sides of the bottom tooth cover 60.

Additionally, the end portion of the third driving rod 90 comprises four isolation rods, wherein two top isolation rods 91 are combined with the outer right sides of the joint plate 51 of the top tooth cover 50, and wherein two bottom isolation rods 92 are combined with the outer right sides of the joint plate 61 of the bottom tooth cover 60.

Each of the driving rods 70, 80 and 90 brushes the inner side of the teeth when the first driving rod 70 moves up, and brushes the outer side of the teeth when the second and the third driving rods 80 and 90 move down.

When the first driving rod 70 moves down for brushing the inner side of the teeth to the downward direction, the second and the third driving rods 80 and 90 move up for brushing the teeth to the upward direction. Therefore, the teeth are brushed up and down direction in crossing.

Driving the first driving rod 70 to the opposite direction of the second and the third driving rods 80 and 90 performs such brushing operation for the teeth. To perform such a cross-driving method, a first elevation means is prepared in the inside of the handle 10 for elevating the first driving rod 70, and a second elevation means is also prepared in the inside of the handle 10 for elevating the second and the third driving rods 80 and 90.

Referring to FIG. 6 to FIG. 10, more detailed explanation will be given as follows.

Each of the elevation means is installed in the inside of the handle 10 to be driven. For this, a motor 20 for generating a driving force is installed in the backside of the inside of the handle 10. In more, the front side of the handle 10 comprises a penetration hole 11 in rectangular shape penetrated by each of the driving rods 70, 80 and 90.

The motor 20 comprises a rotation axis 21 prolonged to the front side of the handle 10. The rotation axis 21 comprises 2 eccentric units 23 and 24, wherein each of the eccentric units 23 and 24 comprises a first elevation means and a second elevation means, respectively.

The first eccentric unit 23 is formed in the front side of the rotation axis 21, and is bent in rectangular shape to one direction. The second eccentric unit 24 is formed in the rear side of the rotation axis 21, and is bent in rectangular shape to the other direction. In the inside of the handle 10 connected to the end portion of the rotation axis 21, a bearing(not shown) is installed to support the rotation axis 21.

Additionally, the first elevation means comprises a first elevation ring 25 and a first extension rod 27. The first elevation ring 25 in rectangular shape includes a long hole to a side direction for fitting to the first eccentric unit 23. In more, the first extension rod 27 is connected to the center of the first elevation ring 25, and the upper inside of the handle 10 supports the upper end of the first extension rod 27. In more, the first extension rod 27 is connected to the first driving rod 70. The first extension rod 27 has a general piston structure.

Sequentially, the second elevation means comprises a second elevation ring 26 and a second extension rod 28. The second elevation ring 26 in rectangular shape includes a long hole to a side direction for fitting to the second eccentric unit 24. In more, the second extension rod 28 is connected to the center of the second elevation ring 26, and the upper inside of the handle 10 supports the upper end portion of the second extension rod 28. The second extension rod 28 also has a general piston structure like the first extension rod 27.

In both insides of the handle 10, a guide projection 29 is formed in vertical shape to guide up/down sliding movement of the first elevation ring 25 and the second sliding rod 26. In more, in the guide projection 29, a first guide groove 30 prolonged to up/down direction is formed to fit on the side of the first elevation ring 25, and a second guide groove 31 is formed to fit on the side of the second elevation ring 26 in the rear portion of the first guide groove 30.

In more, it is preferable to coat a fabrication material such as Teflon for elevating easily the elevation rings 25 and 26 fitted into the corresponding guide grooves 30 and 31, respectively.

On the contrary, the elevation means gets other embodiments differed from the above described embodiment by applying a static rotatable motor 20.

Figure 11:
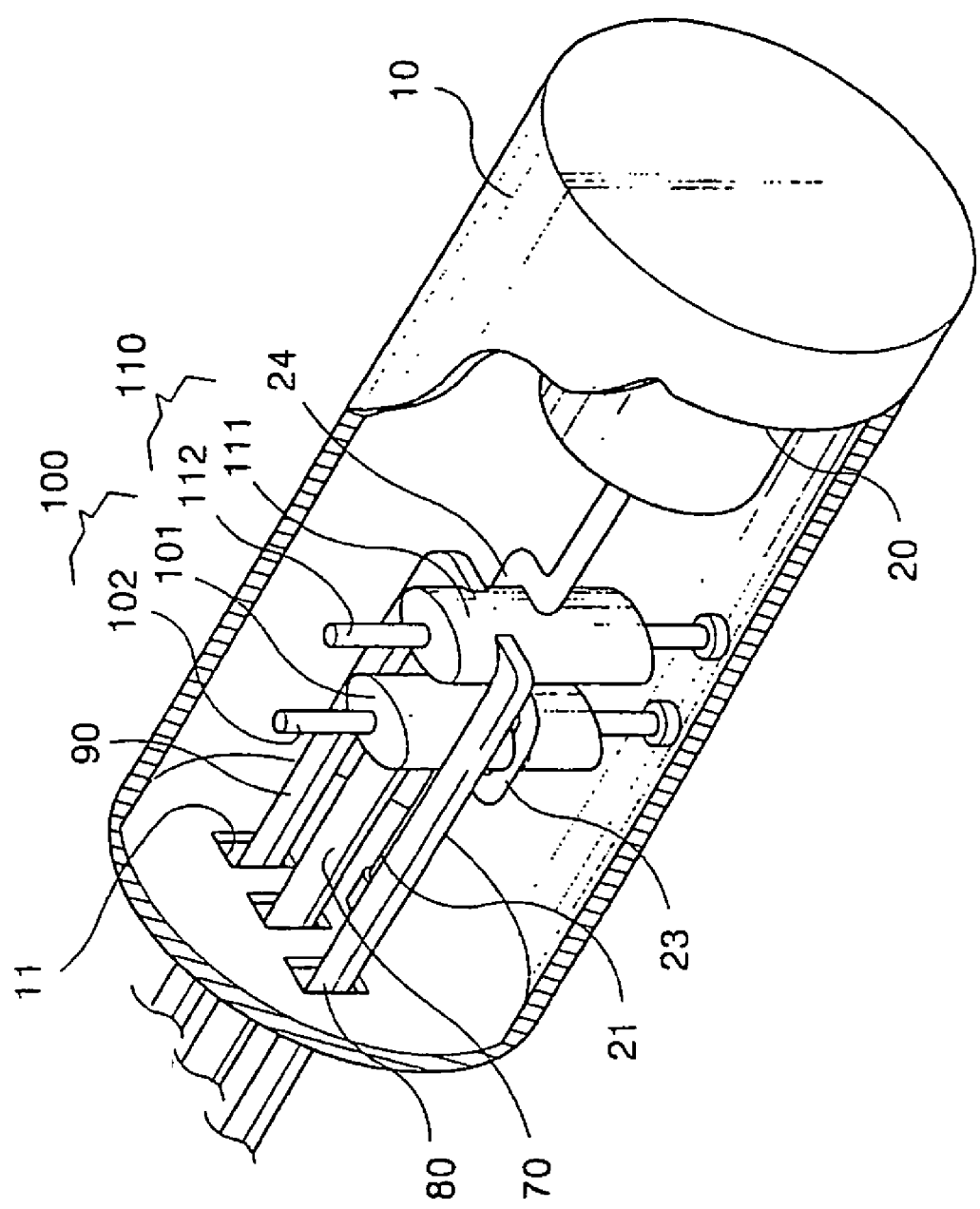
FIG. 11 is a perspective view for driving rods of the electro-motion toothbrush according to another preferred embodiment of the present invention.
Figure 12:
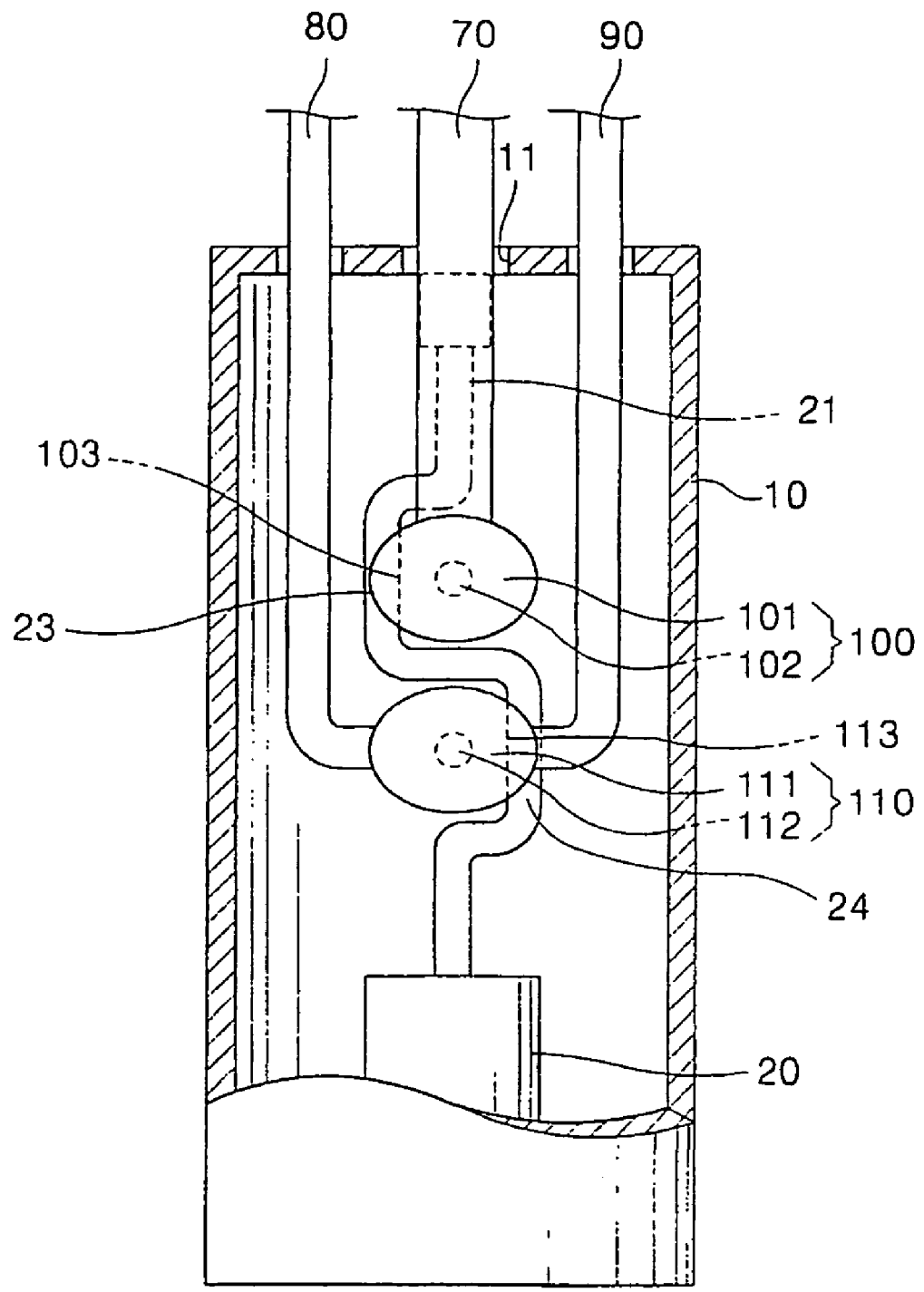
FIG. 12 is a cross sectional diagram illustrating operation states of the electro-motion toothbrush of FIG. 11.

Other preferred embodiments of the elevation means are illustrated in FIG. 11 and FIG. 12. As shown in FIG. 11 and FIG. 12, according to other preferred embodiments of the present invention, the first elevation means includes a first elevation piston 100 fitted on the inner circle of the first eccentric unit 23 of the rotation axis 21, and the second elevation means includes a second elevation piston 110 fitted on the inner circle of the second eccentric unit 24.

In more, the first elevation piston 100 connected to the first driving rod 70 includes a first elevation cylinder 101 and a piston rod 102. To the side of the first elevation cylinder 101 in oval shape, the first eccentric unit 23 fits on a supporting groove 103. The piston rod 102 inserted into the up/down side of the first elevation cylinder 101, and makes the first elevation cylinder 101 move up/down while both outside end portions of the first elevation piston 100 are supported by the top and the bottom side of the handle 10, respectively.

In more, the second elevation piston 110 connected to the second and the third driving rods 80 and 90 includes a second elevation cylinder 111 and a piston rod 112. To the side of the second elevation cylinder 111 in oval shape, the second eccentric unit 24 fits on a supporting groove 113. The piston rod 112 inserted into the up/down side of the second elevation cylinder 111, and makes the second elevation cylinder 111 move up/down while both outside end portions of the second elevation piston 110 are supported by the top and the bottom sides of the handle 10, respectively.

Therefore, when the motor 20 is rotated in a predetermined degree in static state, the first eccentric unit 23 and the second eccentric unit 24 perform static rotations repeatedly and continuously. Accordingly, the first elevation cylinder 101 is moved up/down in an opposite direction with the second elevation cylinder 111. As a result, the first driving rod 70 moves up and down repeatedly in an opposite direction with the second and the third driving rods 80 and 90.

In following statements, it will be illustrated the operation states of the electro-motion toothbrush according to the present invention.

Figure 13:
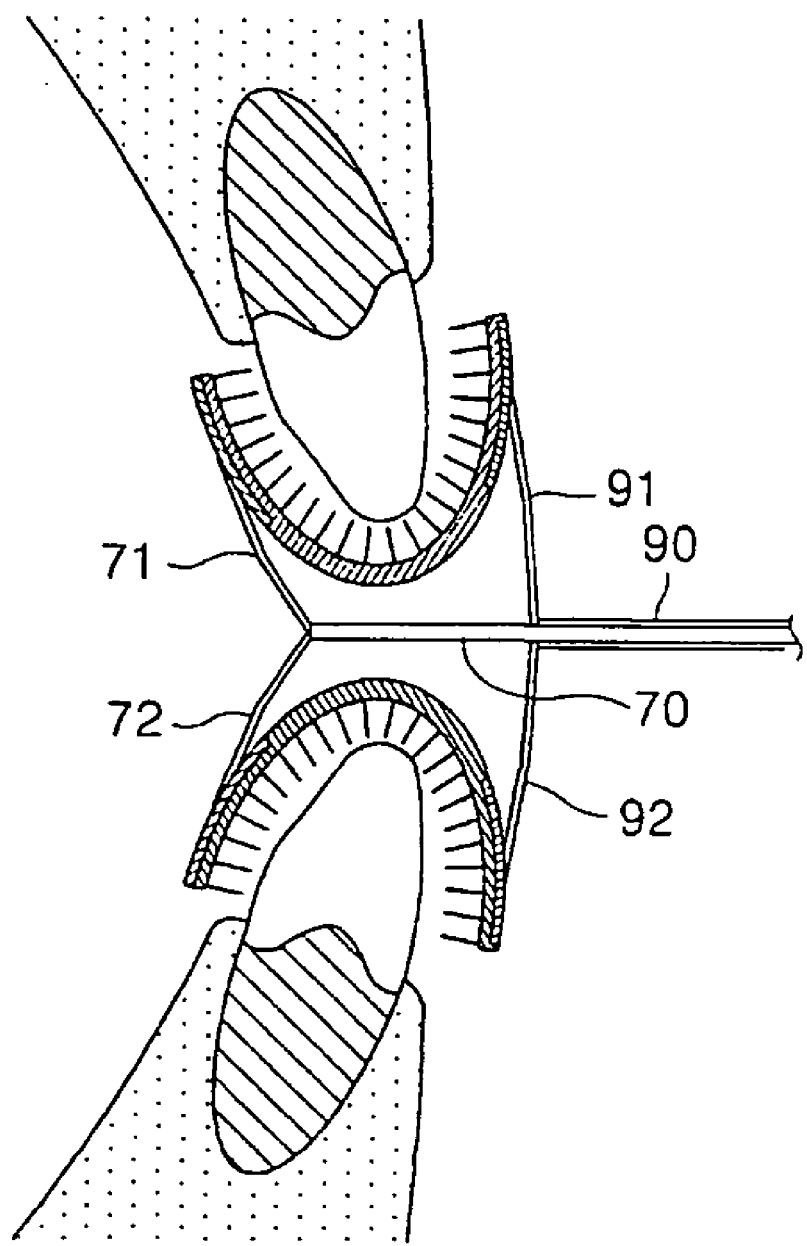
FIG. 13 is an axis cross sectional diagram illustrating the states that a tooth cover of the electro-motion toothbrush is touched with the teeth according to the present invention.

In the electro-motion toothbrush of the present invention, a user grips the handle 10, puts the top tooth cover 50 and the bottom tooth cover 60 into a user's mouth, and fits the top tooth cover 50 on the top maxillary teeth and the bottom tooth cover 60 on the mandibular teeth, as shown in FIG. 13.

Sequentially, when the user turns on a switch 12 of the handle 10, the motor 20 inside of the handle 10 starts to rotate the rotation axis 21. The first eccentric unit 23 and the second eccentric unit 24 are also rotated according to the rotation of the rotation axis 21.

Figure 7:
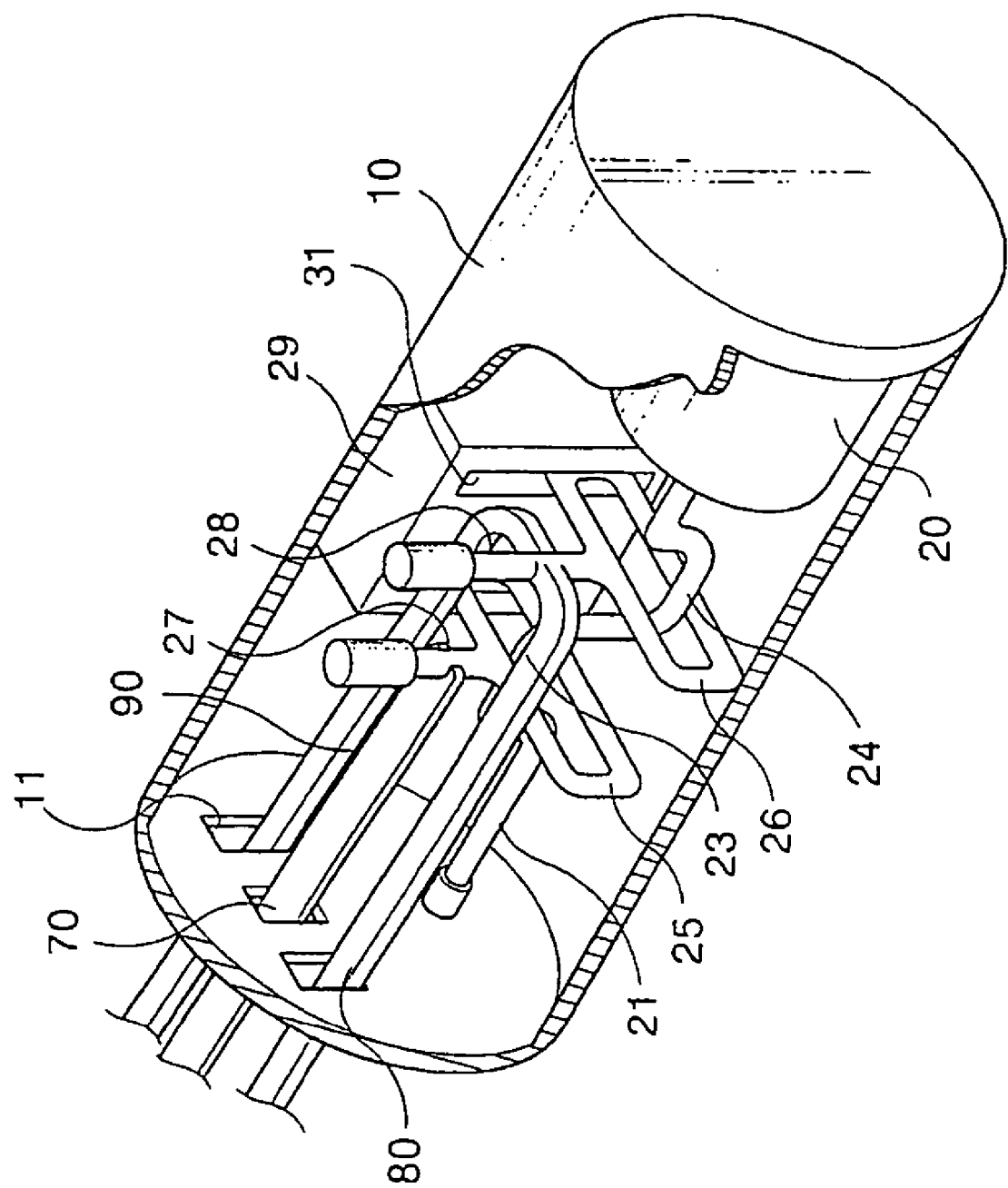

Referring to FIG. 7, when the first eccentric unit 23 rotates, the first elevation ring 25 installed in the first eccentric unit 23 slides to the upward direction, and the first extension rod 27 is contracted. At the same time, the first driving rod 70 installed in the first extension rod 27 also moves to the upward direction. When the first driving rod 70 moves to the upward direction, the insides of the top tooth cover 50 and of the bottom tooth cover 60 also move to upward direction for cleaning the inside of the teeth.

Simultaneously, the second elevation ring 26 of the first eccentric unit 23 moves to the downward direction, and thereof the second extension rod 28 is extended. When the second extension rod 28 is extended, the second and the third driving rods 80 and 90 move to the downward direction, and thereof the outsides of the top tooth cover 50 and the bottom tooth cover 60 move to the downward direction for cleaning the outside of the teeth.

Figure 8:
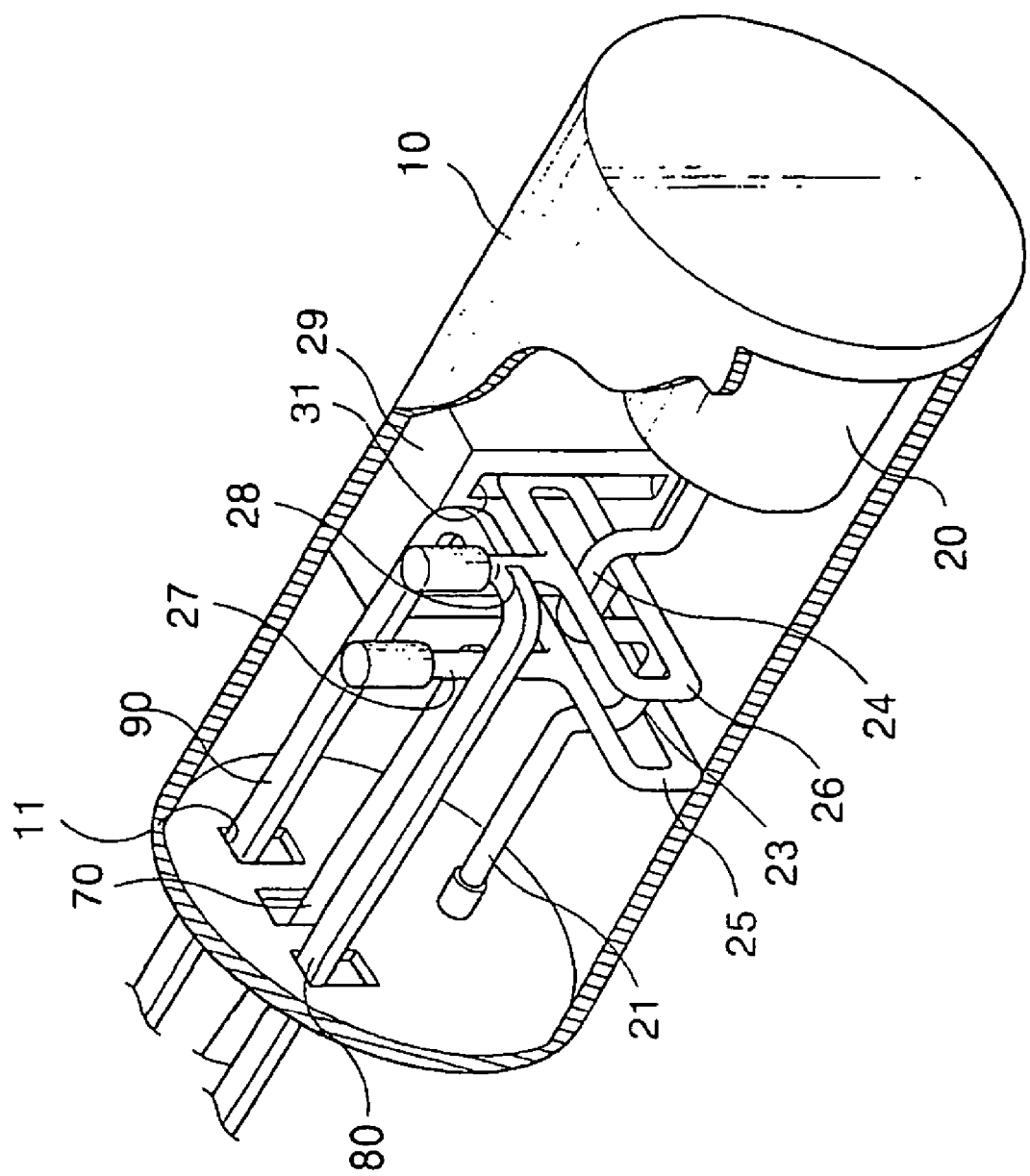
Figure 9:
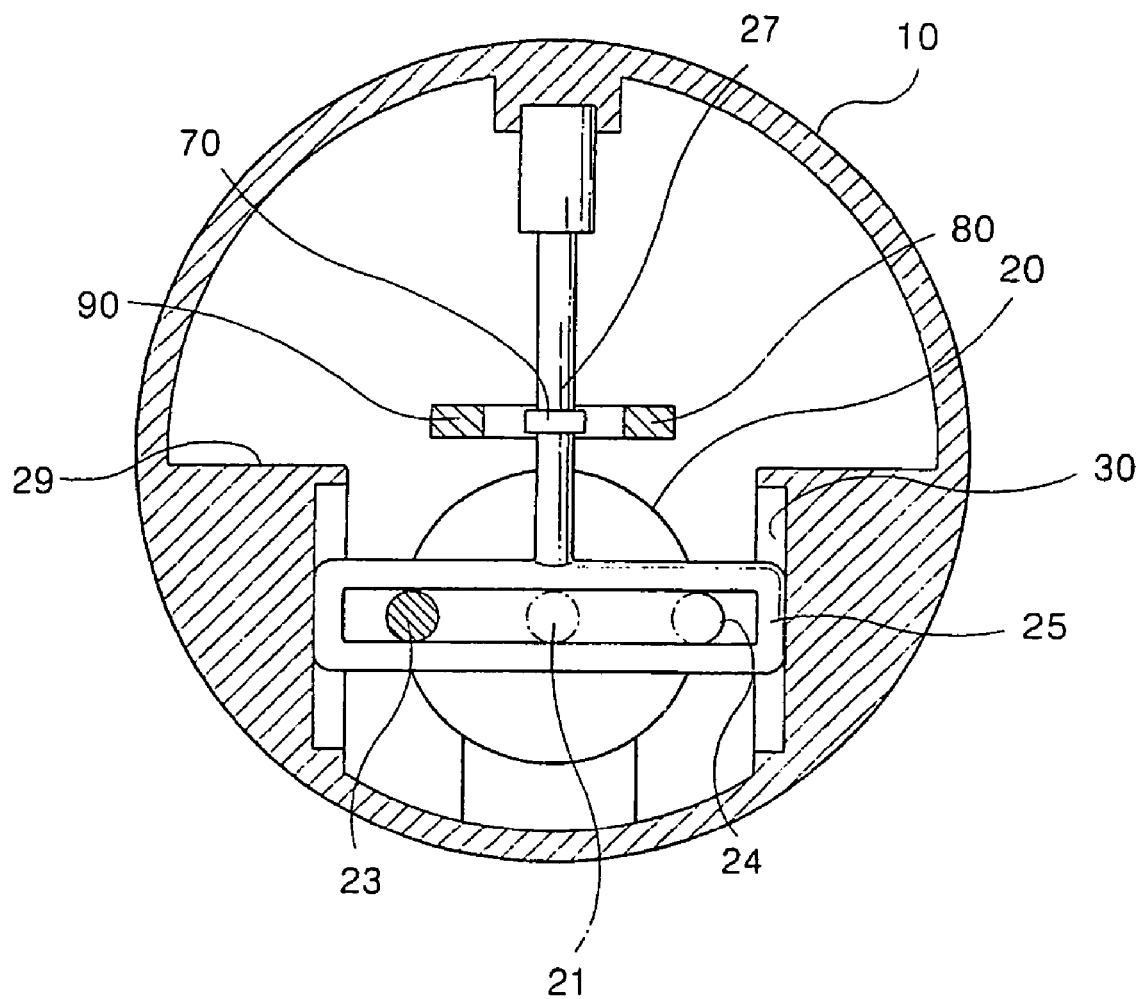
FIG. 9 is a cross sectional diagram of a handle of the electro-motion toothbrush according to the present invention.
Figure 10:
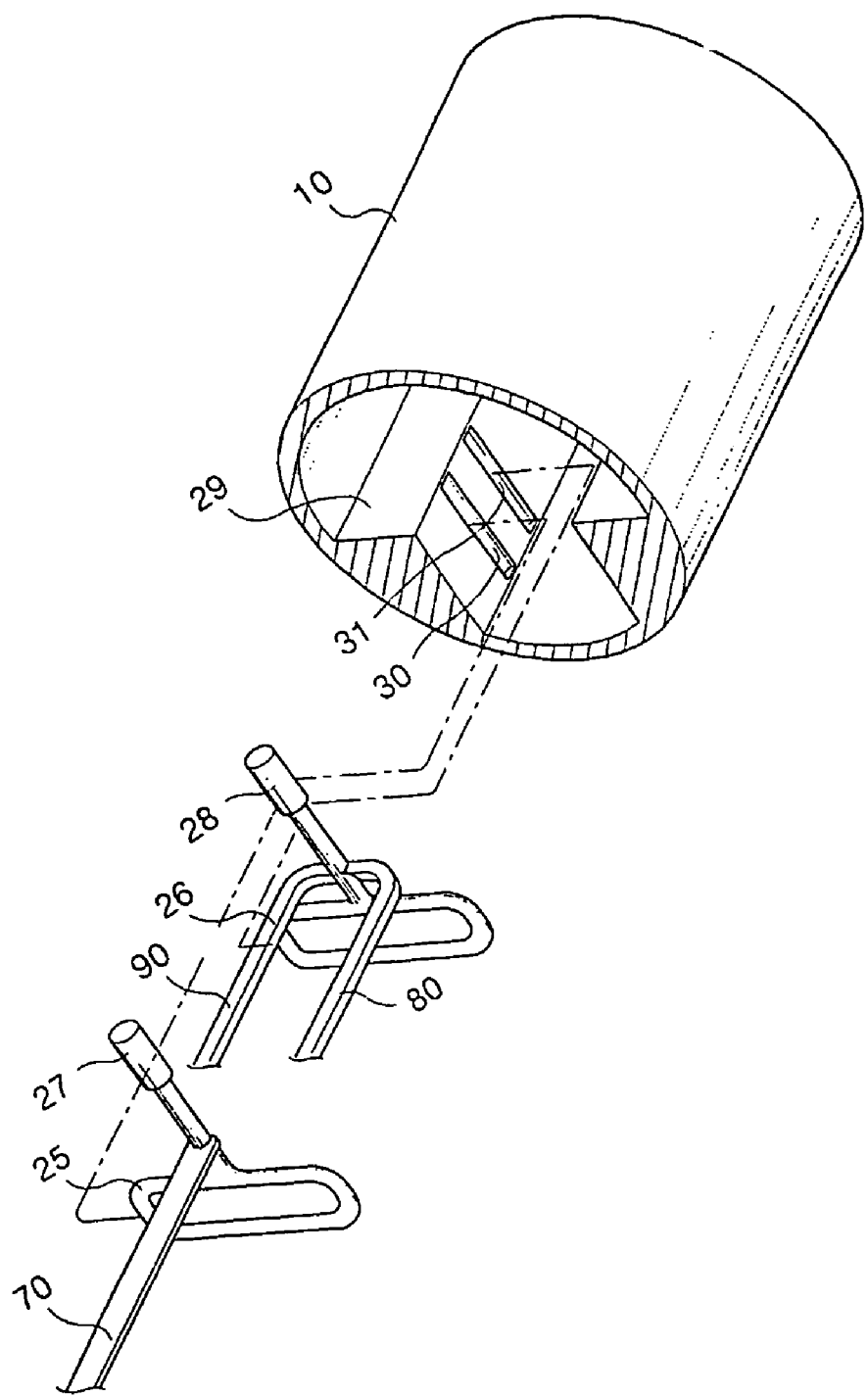
FIG. 10 is a magnified detail cross sectional perspective view of the handle of the electro-motion toothbrush according to the present invention.

Sequentially, when the rotation axis 21 rotates as shown in FIG. 8, the first extension rod 27 is extended to the downward direction—the opposite direction of the above described case—by the first eccentric unit 23, and the second extension rod 28 is contracted to the upward direction. Therefore, the first driving rod 70 combined with the first extension rod 27 moves to the downward direction, and the insides of the top and the bottom tooth cover 50 and 650 move to the downward direction while cleaning the insides of the teeth.

Additionally, as the second extension rod 28 is contracted to the upward direction, the second and the third driving rods 80 and 90 move to the downward direction, and the outsides of the top and the bottom tooth covers 50 and 60 move to the upward direction while cleaning the outside of the teeth.

In repeating such operations, the top and the bottom tooth covers 50 and 60 clean the inside and the outside of the teeth, and perform tooth brushing to the teeth automatically.

The joint plates 51 and 61 of the top and the bottom tooth covers 50 and 60 installed in each of the driving rods 70, 80 and 90 are apart among them about 1~2 mm. Therefore, when the top and the bottom tooth covers 50 and 60 move up and down, tooth brushing is performed to the gap of the teeth in flexible. In more, when the bristles 59 is varied in length according to the location and the shape of the teeth, such as a molar and a foretold, tooth brushing can be performed efficiently.

Additionally, for cleaning the teeth smoothly, it is preferable that contact points of the tooth covers 50 and 60 are apart from the teeth-ridge about 1 mm.

In the second preferred embodiment of the present invention, when the motor 20 rotates in static state in a predetermined degree, the first elevation piston 100 combined with the first eccentric unit 23 contracts in one direction, and the second elevation piston 110 combined with the second eccentric unit 24 contracts in the other direction.

Because each of the eccentric units 23 and 24 is fitted on and frictionized with the supporting grooves 103 and 113 formed in the outsides of each of the corresponding elevation pistons 100 and 110, it is preferable to coat a fabrication material such as Teflon on the friction points.

Therefore, each of the elevation pistons 100 and 110 moves up and down in repeat and in the opposite direction between each other. In more, the first driving rod 70 moves to the opposite direction to the second and the third driving rods 80 and 90 for teeth brushing.

As another modified embodiment of the present invention, two driving motors are equipped, and each of the eccentric units is installed to each of the rotation axes of the corresponding driving motor in separate. Therefore, safer operation can be performed. Additionally, each of the driving rods can be projected to the side of the handle by modifying the installation states to make the user grip the electro-motion toothbrush of the present invention from a left or a right direction for cleaning his teeth.

In the configuration according to the above described embodiment of the present invention, the top and the bottom tooth covers 50 and 60 can be shaped to fit on the teeth of a user according to the user's order. In this case, the terminals of the top and the bottom tooth covers 50 and 60 can be closed to form a single body, and the bristles can be implanted into the closed points. In more, in the case of manufacturing in order, the bristles located between the teeth can be longer than those located in other parts or teeth to brush the gap between the teeth better.

In more, various standards of the toothbrush can be produced in mass according to the ages and the physical figures for normal usages.

To supply the electro-motion toothbrush of the present invention economically, one tooth cover is only manufactured. In more, after installing the inner driving rod combined with the inside of the tooth cover, and the outer driving rod combined with the outside of the tooth cover, each of the driving rods moves in the opposite direction between each other. It can be actualized by applying the modified elevation means of the above described embodiment.

Additionally, for more practical use, an inner electric power can be equipped in the inside of the electro-motion toothbrush, and an outer electric power can be connected to the electro-motion toothbrush. A recharge battery can also supply an electric power. All of the powers can be applied together or in separate.

For improved operations, When a shape memory alloy, an enhancing material with a width of 2~3 mm, is installed in both sides of the electro-motion toothbrush contacted with the molars, the electro-motion toothbrush can be operated in smooth and firm. Referring to FIG. 4c, the shape memory alloy can be molded with the tooth covers 50 and 60.

On the contrary, as another embodiment of the present invention, the tooth covers 50 and 60 of the electro-motion toothbrush of the present invention can be abraded and deformed. In this case, it is preferable to change the tooth covers 50 and 60. To change the tooth covers 50 and 60, the middle of the driving rods 70, 80 and 90 is intersected to assemble the driving rod of the handle 10 with the driving rod of the tooth covers 50 and 60.

Figure 14:
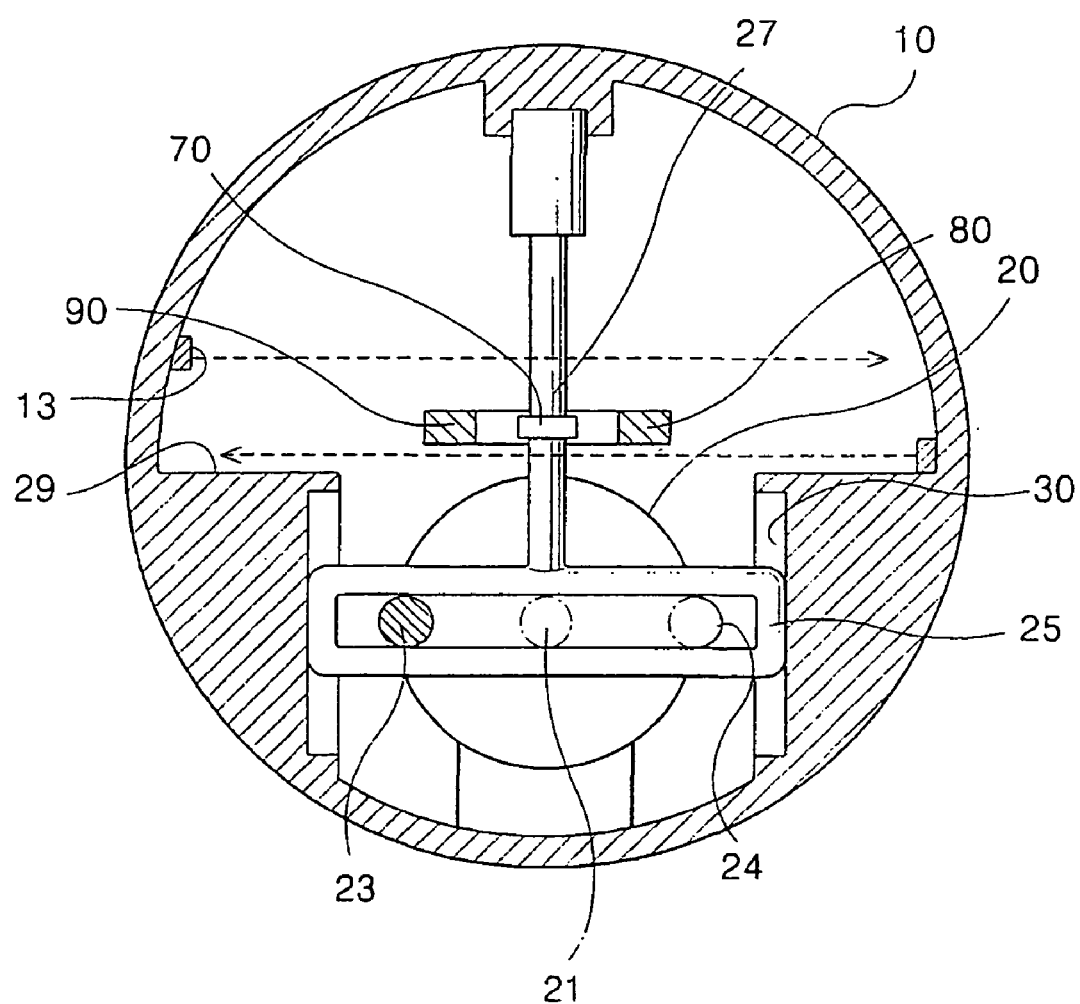
FIG. 14 is a cross sectional diagram for the handle of the electro-motion toothbrush according to another preferred embodiment of the present invention.
Figure 15:
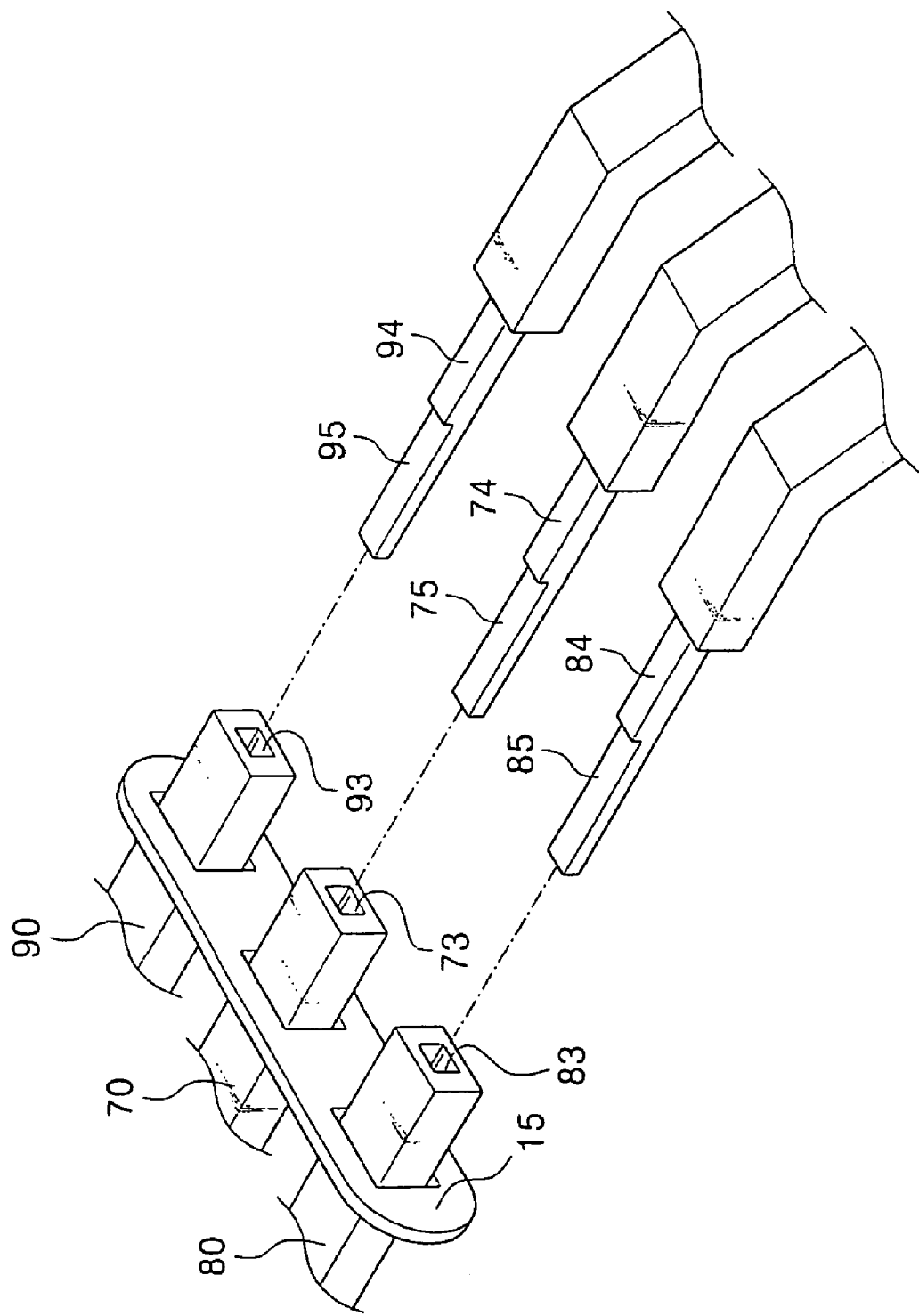
FIG. 15 is a detail perspective view illustrating a detachable tooth cover of the electro-motion toothbrush according to the present invention.
Figure 16:
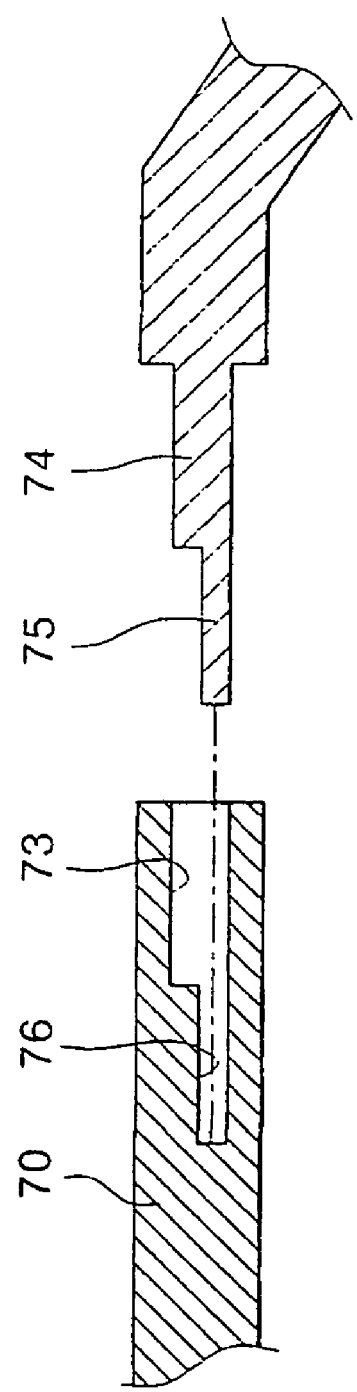
FIG. 16 is a cross sectional diagram illustrating a detachable tooth cover of the electro-motion toothbrush according to the present invention.

Replacing the tooth covers 50 and 60 can be accomplished as follows. When the switch 12 is positioned in the arrange mode, two photo sensors 13 detect the positions of each of the driving rods 70, 80 and 90 installed in the inside of the handle 10, as shown in FIG. 14. In other words, one of the driving rods 70, 80 and 90 is in the upper or the lower position, the motor 20 controls automatically to locate three driving rods 70, 80 and 90 in horizontal among them.

In this horizontal states, the user can buy separately and assemble the tooth covers 50 and 60. A joint ring 15, including three horizontal holes, supports the driving rods 70, 80 and 90 of the tooth covers 50 and 60 purchased separately. Therefore, when the tooth covers 50 and 60 are assembled, the insertion rods 74, 84 and 94 formed in the driving rods 70, 80 and 90 of the handle 10 are fitted on the insertion holes 73, 83 and 93 of the tooth covers 50 and 60 simultaneously The cross sections 75, 85 and 95 of the insertion rods 74, 84 and 94 are inserted into and assembled with the stepped unit 76 of the inside of the insertion holes 73, 83 and 93. Therefore, the firm assembly is accomplished.

On the contrary, to maintain firm joint states, the inside of the insertion holes 73, 83 and 93 becomes narrower from entrance in depth. Therefore, the insertion rods 74, 84 and 94 can be squeezed firmly in the inside of the insertion holes 73, 83 and 93. Additionally, the insertion rods 74, 84 and 94 and the insertion holes 73, 83 and 93 can be embodied in various shapes. When the insertion rods 74, 84, and 94 are fitted on the insertion holes 73, 83 and 93, the joint ring 15 is separated, and thereafter the electro-motion toothbrush can be used.

As described in the above statements, a portion of the configuration of the electro-motion toothbrush according to the present invention can be modified according to the application necessity. However, when such modified embodiment of the electro-motion toothbrush includes tooth covers moving up and down in opposite direction between each other, and multiple driving rods and elevation means for driving the tooth covers, the modified embodiment will belong to the technical ranges of the present invention.

The electro-motion toothbrush of the present invention drives the inside and the outside of the tooth covers, covering the whole teeth, to the opposite direction between each other to clean the teeth automatically and fully. Therefore, simple and easy cleaning for the teeth can be accomplished.

While the invention has been particularly shown and described with reference to preferred embodiments thereof, it will be understood by those skilled in the art that the foregoing and other changes in form and details may be made therein without departing from the spirit and scope of the invention.

What is claimed is:

1. An electro-motion toothbrush comprising:
    an upper tooth cover surrounding and covering the upper teeth having a first inner and a first outer surface, the first inner surface has bristles formed at a surface contacting the teeth;
    a lower tooth cover surrounding and covering the lower teeth having a second inner and a second outer surface, the second inner surface has bristles formed at a surface contacting the teeth;
    a first driving rod combined with the first and second outer surfaces of the upper and lower tooth covers;
    a second driving rod combined with a left side of the first and second outer surfaces of the upper and lower tooth covers;
    a third driving rod combined with a right side of the first and second outer surfaces of the upper and lower tooth covers;
    a plurality of sensors, independently sensing positions of the first, second, and third driving rods;
    reciprocating means driving the first driving rod and the second and third driving rods in opposite directions to move the upper and lower tooth covers in opposite directions and thereby clean the teeth, the reciprocating means driven by power supplied from a motor, in response to position information sensed by the plurality of sensors.

2. The electro-motion toothbrush according to claim 1, wherein the upper and lower tooth covers includes a joint plate combined with the first driving rod, the second driving rod, and the third driving rod.

3. The electro-motion toothbrush according to claim 1, wherein the upper and lower tooth covers include a plurality of bristle plates adhesively combined together, each of the plates implanted with bristles.

4. The electro-motion toothbrush according to claim 1, wherein concave regions of the top and the bottom tooth covers include projection regions for making the bristles contact with molars of the teeth.

5. The electro-motion toothbrush according to claim 1, wherein the motor and the reciprocation means are provided inside a handle, and the reciprocation means comprises:
    a first reciprocation means disposed on the axis of rotation of the motor and reciprocating the first driving rod up and down when, the motor rotates; and a second reciprocation means disposed on the axis of rotation of the motor and reciprocating the second and the third driving rods up and down in the opposite direction to the first driving rod when the motor rotates.

6. The electro-motion toothbrush according to claim 5, wherein the rotation axis of the motor comprises:
    a first eccentric unit, bent in one direction and rotated eccentrically, providing an eccentric force to the first reciprocation means; and
    a second eccentric unit, bent in the other direction and rotated eccentrically, providing an eccentric force to the second reciprocation means.

7. The electro-motion toothbrush according to claim 6, wherein the first reciprocation means comprises:
    a first reciprocation ring, including a long hole extending in one direction into which the first eccentric unit fits; and
    a first extension rod extending from the first reciprocation ring, supported by the inside of the handle, and combined with the first driving rod,
    and wherein the second reciprocation means comprises:
    a second reciprocation ring including a long hole extending in one direction into which the second eccentric unit fits; and
    a second extension rod extending from the second reciprocation ring, supported by the inside of the handle, and combined with the second and the third driving rod.

8. The electro-motion toothbrush according to claim 7, wherein the first and second reciprocation rings are provided inside the handle, and first and second guide grooves are provided at both ends of the first and second reciprocation rings for guiding up/down movement of the first and the second reciprocation rings.

9. The electro-motion toothbrush according to claim 7, wherein the first and second reciprocation rings are provided inside the handle, and the first reciprocation means includes a first piston extendable in both directions according to direction of reciprocation, both ends of the first piston supported by the inside of the handle, and the first eccentric unit being fitted on the side of the first piston; and wherein the second reciprocation means includes a second piston extendable in both directions according to direction of reciprocation, both ends of the second piston are supported by the inside of the handle, and the second eccentric unit being fitted on the side of the second piston.

10. The electro-motion toothbrush according to claim 6, wherein the motor is a static rotation motor.

11. The electro-motion toothbrush according to claim 1, wherein the first driving rod includes:

a plurality of first upper branch rods combined with an inside surface of the tooth cover; and a plurality of first lower branch rods combined with an inside surface of the lower tooth cover.

12. The electro-motion toothbrush according to claim 1 or 8, wherein the second driving rod includes a second upper branch rod combined with a left outside of the upper tooth cover, and a second lower branch rod combined with a left outside of the lower tooth cover, and wherein the third driving rod includes a third upper branch rod combined with a right outside of the upper tooth cover, and a third lower branch rod combined with a right outside of the lower tooth cover.

13. The electro-motion toothbrush according to claim 1, wherein a middle portion of each of the first, second, and third driving rods is divided into a plurality of sections and are combined with the upper and lower tooth covers.

* * * * *